United States Patent
Růžička et al.

(10) Patent No.: US 8,529,489 B2
(45) Date of Patent: Sep. 10, 2013

(54) METHOD TO SUPPRESS BLOOD COAGULATION IN THE CIRCUIT OF THE DEVICE SUBSTITUTING THE KIDNEY FUNCTION AND APPARATUS REALIZING THIS METHOD

(75) Inventors: Jiří Růžička, Plzeň (CY); Zuzana Petránková, Veltruby (CZ); Jiří Beneš, Plzeň (CZ); Lukáš Bolek, Plzeň (CZ); Aleš Krouzecký, Letkov (CZ); Roman Sýkora, Plzeň (CZ); Martin Matějovič, Plzeň (CZ)

(73) Assignee: Univerzita Karlova V Praze, Pizen (CZ)

( * ) Notice: Subject to any disclaimer, the term of this patent is extended or adjusted under 35 U.S.C. 154(b) by 186 days.

(21) Appl. No.: 12/320,276

(22) Filed: Jan. 22, 2009

(65) Prior Publication Data

US 2010/0114003 A1  May 6, 2010

(30) Foreign Application Priority Data

Jan. 22, 2008 (CZ) ........................................ 2008-35

(51) Int. Cl.
*A61M 37/00* (2006.01)

(52) U.S. Cl.
USPC ............................................. 604/6.13

(58) Field of Classification Search
USPC ...... 604/4.01–6.16, 95.01–96.01; 422/44–48
See application file for complete search history.

(56) References Cited

U.S. PATENT DOCUMENTS 4,894,164 A * 1/1990 Polaschegg ............ 210/646
2006/0210424 A1 * 9/2006 Mallett et al. ............. 422/44

FOREIGN PATENT DOCUMENTS

| EP | 1 132 101 A1 | 9/2001 |
| EP | 1 261 413 A1 | 12/2002 |
| EP | 1 623 733 A2 | 2/2006 |

OTHER PUBLICATIONS

Otte, K.E. et al., "Heparin-Free Hypothermal Hemodialysis at 20° C. Improves Biocompatibility." Blood Purification, vol. 15, No. 3, 1997.*

K.E. Otte, et al., Heparin-Free Hypothermal Hemodialysis at 20° C. Improves Biocompatibility, Blood Purification 1997:15:200-207. Denmark.

Michael J. Rohrer, MD et al., Effect of Hypothermia on the Coagulation Cascade, Critical Care Medicine, 1992 by Williams & Williams, vol. 20, No. 10, pp. 1402-1405.

* cited by examiner

*Primary Examiner* — Philip R Wiest

(74) *Attorney, Agent, or Firm* — Buchanan Ingersoll & Rooney PC

(57) ABSTRACT

A method and device for reducing blood coagulation in the circuit of a device for substitution of the kidney function wherein, prior to the input in the device for substituting the kidney function, the blood which left the patient's body is cooled down to a temperature in the range 10° C. to 30° C. and, as the blood passes the device for substitution of the kidney function, that blood is warmed up to a temperature at least near to the body temperature and then it is returned in the patient's body.

10 Claims, 1 Drawing Sheet

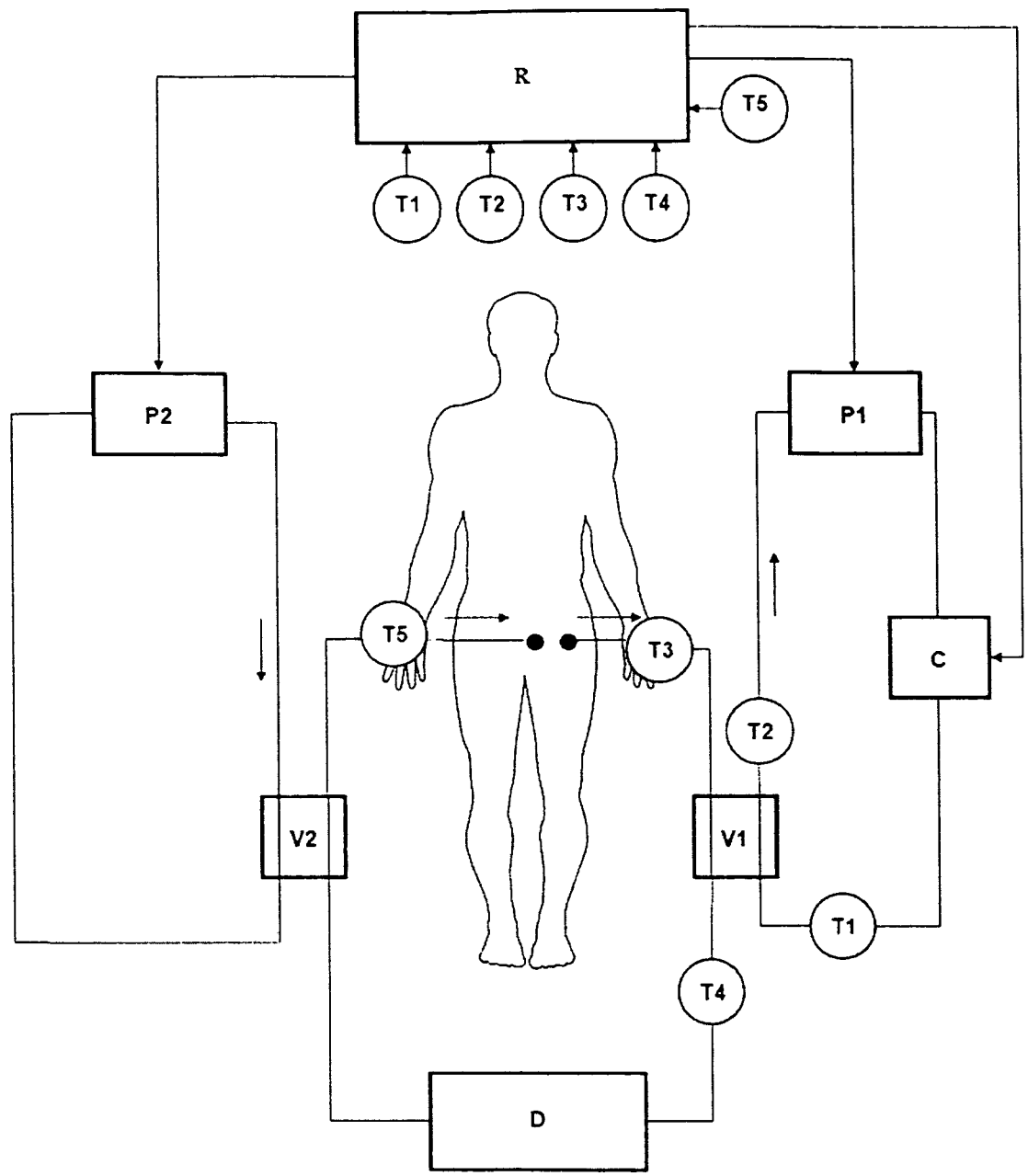

METHOD TO SUPPRESS BLOOD COAGULATION IN THE CIRCUIT OF THE DEVICE SUBSTITUTING THE KIDNEY FUNCTION AND APPARATUS REALIZING THIS METHOD

TECHNICAL FIELD OF THE INVENTION

The invention is a procedure diminishing the blood coagulation in the circuitry of the device substituting the kidney function and a device performing this procedure.

BACKGROUND OF THE INVENTION

Contemporary medicine employs devices substituting the kidney function either for intermittent treatment, where the patient is connected with the device periodically in seances lasting several hours, or continuously, where the patient is connected with the device permanently. In either case there must be prevented blood coagulation in the capillary channels of the device filter and in other extracorporeal parts of the blood circuit. Usually in these cases the coagulation of blood is prevented by systemic supply of anticoagulation drugs which is accompanied with some hazard especially in patients with complex disorders. As alternatives there are sometimes employed: regional anticoagulation, adding anticoagulants, usually sodium citrate, then minimum systemic anticoagulation (using heparin and/or prostaglandins), or we get without of any anticoagulant and only flush the system with saline in regular intervals. No of the above said procedures is satisfactory and all are connected with some hazard for the patient, as e. g. metabolism alteration, bleeding or inadequate anticoagulation. In addition, improper anticoagulation measures, even when it does not cause instantaneous coagulation in the device circuitry, it can activate the cascades of coagulation steps and so alter the fragile and often just changed coagulation equilibrium. There must also be considered useless elevation of the cost of extracorporeal blood cleansing by frequent exchanges of sets and filters.

It is known that decrease of blood temperature inhibits enzymatic reactions in the coagulation cascade and deactivates primary hemostasis and also the coagulation process itself, as described e. g. in Rohrer M J, Natale A M, Crit Care Med, 1992 October; 20 (10): 1402-5.

In sufficiently low temperature the blood may become completely unable to coagulate. Hence appears the not yet tried possibility to employ cooling as an anticoagulation agent. The blood which left the patient body is first cooled and only thereafter it is led into the device substituting the kidney function and on the output of the device the blood is warmed up and led in the patient body.

This coagulation preventing method has just been tried successfully in experiments in animals—in pigs a three hours intermittent dialysis was applied where the blood in the circuit was cooled on 20° C. and before the return in the body it was rewarmed on 37° C. No traces of hemolysis could be observed which could be theoretically caused by sudden temperature changes (Otte K E et all., Blood Purif. 1997, 15: 200-207). But this research mainly tried to influence the compatibility between extracorporeal blood flow and life and observed only if the extracorporeal ways remained passable but did not examine in them any changes of blood coagulation or inactivation of coagulation and fibrinolytic processes. In addition, these authors followed the effectiveness of this method in intermittent extracorporeal method only, but not in the continuous one, in which the coagulation might be more apparent. Also the technical realization of the device was different; the blood was not cooled directly but only by the contact with the dialytic solution after its passage through a hose submerged in a vessel containing ice and water. For warming up served a microwave oven. Automatic control of the process was not tried here and the process did not fulfill even the most basic security parameters which could make possible to consider its clinical application for patients.

In blood passing through the device substituting the kidney function substances are exchanged between blood and dialytic solution over the semipermeable membrane, controlled by physical laws of the diffusion process. It is known that diffusion through a membrane is temperature dependent so that the temperature rise raises amounts of substances transported by diffusion. The EP1261413A1 patent uses this phenomenon letting the blood to pass two dialytic filters. In the first one the dialytic solution temperature is raised and the dialysis takes place under elevated temperature. In the second one the dialytic solution temperature is again decreased and hence the blood is cooled to the body temperature. The question is, if temperature rise above the normal body temperature in the first filter will not increase the activity of the coagulation processes in the circulating blood. The essence of the presented solution is reversed effect on the blood, i.e., its cooling prior to the input into the device substituting the kidneys. Because of the temperature dependence of diffusion rate—see above—we can anticipate that the dialysis in this arrangement could be less efficient. But this disadvantage cannot be considered too relevant, esp. in the regimen of continuous treatment, where there is the blood mainly filtered, i.e. certain volume of plasma is removed and is replaced by the substituting solution. The dialysis proper is minimum involved.

Blood temperature is often manipulated in heart surgery, in surgery employing extracorporeal circulation, where the cooling of the patient's body renders the operations on open heart technically possible. The aimed body temperature, to which is the patient cooled, is different depending on surgery type with the bottom temperature limit 16 to 17° C. For the cooling and reheating of the patient are used filters which in more modern devices are combined with the oxygenator where the impermeable capillaries are cooled/heated by the cooling/heating medium running over them, or in more ancient apparatuses also separate devices where the blood which passed the oxygenator before its return into the patient flows through the filter/exchanger, where it gets in contact with the cooling/heating medium. Purpose of these devices—see e.g. patent EP1623733A2—is to manipulate the temperature of the whole patient, not to precisely adjust the temperature of his blood. The temperature is affected e.g. so that in the process of cooling the patient there is set the temperature of the cooling medium, not that of the blood, and this temperature of the coolant is set by a certain difference lower than the patient's body temperature and the warming up runs analogously. The process is controlled manually by the physician or by a perfusionist.

Blood temperature is also manipulated in patient's whole body hypothermia or in local hypothermia of brain e.g. in states after successful resuscitation in a patient with a sudden cardiac arrest, where such cooling positively affects possible future neurological deficit. For this purpose there may be used e.g. the device described in EP1132101A1, which enables to maintain temperature of the object in the desired level. In this device the blood of the patient is mixed with a cooled solution and afterwards it is concentrated and so the blood temperature is controlled at the instance of its reentrance into the cooled object.

As described, manipulating the blood temperature we can retard the coagulation processes in the blood. Up to the present time the blood temperature in the extracorporeal circuit was not manipulated for the sake to influence coagulation in the extracorporeal circuit. Yet this not employed possibility of anticoagulation activity seems to be very regardful to the patient. There offers itself the following solution: The blood let out of the patient's body, i.e. before it is led into the device substituting the kidney, is cooled and on the output of this device the blood temperature is raised again and the warmed blood is reintroduced in the patient's body.

SUMMARY OF THE INVENTION

The invention represents a mode to reduce ability of blood to coagulate in the circuit of the device substituting the kidney function. Blood leaving the patient's body prior to its entrance in the device is cooled to temperature between 10 to 30° C. and at the output of the device the blood is reheated to a temperature near to or identical with the body temperature and thereafter it is returned into the patient's body. By this manipulation only of the patient's blood temperature the coagulation processes will be retarded. Hence the described method does not demand any addition of substances with anticoagulation activity and is thus considerate of the patient.

The invention is a device realizing the described mode which contains two heat exchangers, the first one being placed before the device substituting the kidney function. This first heat exchanger is connected to the supply of the cooling medium; the second exchanger is placed behind the device substituting the kidney function and is connected with the heating medium supply It is of advantage when the first heat exchanger is preceded by an input temperature sensor and followed by an output temperature sensor and both sensors are connected with the control unit; the same holds for the temperature sensor placed in the input of cooling medium in the first heat exchanger. Such a setup guarantees perfect temperature control of the cooled blood before it enters the device substituting the kidney function.

Perfect and reliable control of the output temperature in the cooled blood will be achieved when there is also a temperature sensor in the coolant leaving the first heat exchanger, which sensor is also connected with the control unit. This temperature sensor yields information on fluctuations of the coolant temperature at the output, where its sudden change signals e.g. a trouble in blood passage through the device substituting the kidney function.

It is appropriate when the first heat exchanger is located utmost close to the blood output of the patient body. The output is usually secured by a dialysis cannula. In such arrangement there is minimized the risk of blood coagulation after it left the patient's body.

Information about the temperature of the blood leaving the second heat exchanger is given by a temperature sensor located between the exchanger and the patient or a temperature sensor placed in the patient's body, best in one of his body cavities, possibly connected with the control unit.

In the first heat exchanger the cooled blood temperature can be controlled not only by the coolant temperature but also by the speed of the circulating pump in the coolant circuit of the first heat exchanger, the control of which is connected with the control unit.

BRIEF DESCRIPTION OF THE DRAWING

The schematic FIGURE represents a human body in silhouette together with attached device according to the invention; a block diagram.

DETAILED DESCRIPTION OF A SPECIFIC EMBODIMENT

Example 1

The patient is in intensive care following his polytrauma, and following his extensive primary injury he developed the syndrome of multiple organ failure comprising kidney failure, liver dysfunction, and a severe disseminated intravascular coagulation with inclination to spontaneous bleeding. Hence it was necessary to use continuous extracorporeal cleaning by means of the device D substituting the kidney function. But because of multiple bleeding (a complication of consumption coagulopathy accompanying the disseminated intravascular coagulation) there is not possible to use the standard systemic application of heparin or another anticoagulant as a means securing the extracorporeal circuit against coagulation. In respect of patient's serious liver dysfunction even a regional anticoagulation by means of citrate can not be applied. Hence to render anticoagulation, there is applied the method according to the invention of cutting down the blood coagulation in the circuit of the device D substituting the kidney function and the device to perform the said method. As the target temperature to be sensed by the sensor T4 in the blood leaving the first heat exchanger V1 before it enters the device D substituting the kidney function; we set this temperature at 25° C. This temperature was chosen according to analysis of coagulation parameters and making use of the thromboelastograph. Temperature will be evaluated by the control unit R according to information coming of the temperature sensors T1, T2, T3, T4, which serve on the one hand for setting temperature of the coolant in the circuit P1, and on the other hand for control of the coolant flow speed in the circuit P1, which is driven by the pump C. Blood passing the device D substituting the kidney function is again warmed in the second heat exchanger V2 to 37° C. to which end the initiation temperature in the P2 circuit is set on 39° C. by means of the control unit R. At the same time the patient's body temperature is checked by the sensor T5 placed in the patient's urinary bladder and evaluated in the control unit R.

Example 2

The patient ill with a malignant blood disease is being prepared for transplantation of bone marrow. Caused by systemic immunotherapy, sepsis is developing followed by the syndrome of multiorgan failure. Hence there is necessary to continually cleanse the blood by means of the device D substituting the function of kidneys. Because of protracted coagulation times and an insufficient number of blood platelets which are necessary for blood coagulation it is not convenient for the patient to proceed in standard way and give heparin. Therefore to prevent coagulation in the extracorporeal circuit we will use the method according to the invention for reduction of the blood coagulation in the circuit of the device D for substitution of kidney function and an apparatus for implementation of the method. Target temperature of the cooled blood before its input in the device D for substitution of the kidney function we choose 20° C. in respect of the found state of health. The input temperature sensed by the temperature sensor T4 was chosen by analysis of coagulation parameters and using a thromboelastograph and yields sufficient anticoagulation security. In the control unit R we set the temperature of the heating medium in the circuit P2 at 35° C. which according to previous experiments secures temperature of returning blood 33° C. Because the patient is in state of sepsis, despite of the so cool returning blood he has markedly hyperthermic metabolism and his central temperature first remains about 38° C. Later the patient's central temperature (sensed by the temperature sensor T5 placed in his esophagus) decreases. By means of the control unit R and the temperature sensors is the patient's temperature continuously evaluated with the end to maintain the central temperature on the level of about 38° C.

Example 3

The patient is included in a chronical dialysation program, has heparin induced thrombocytopenia and is suffering from chronic hemorrhagic complications which prevent heparin application as an anticoagulant coverage. For the anticoagulant coverage of the extracorporeal circuit we use a procedure according to the invention for reduction of blood coagulation in the circuitry of device D for substitution of kidney function and in the apparatus for implementation of that method. Analyzing coagulation parameters of the patient's blood and using a thromboelastograph it was found that at the blood input in the device D for substitution of kidney function it will be optimum to cool the blood in the heat exchanger V1 to temperature 22° C. For the P2 exchanger is the temperature of the heating medium set on 39° C. which according to realized trials corresponds with the returning blood temperature 37° C. Continual watching of patient's peripheral temperature showed that the returning blood temperature is set appropriately and that it is not necessary to change it during the whole time the extracorporeal blood cleansing is running.

Manipulations of the blood temperature in the circuit of device D substituting the kidney function was tested in a laboratory on pigs. It was ascertained that filtration by means of device D is realizable in temperature range 10 to 30° C., in lower blood temperature is the filtration process effectivity diminished.

We claim:

1. A method for heparin-free reduction of blood coagulation in the continuous circuit of a kidney dialysis device comprising:
    providing a first heat exchanger;
    cooling blood which has left a patient's body using the first heat exchanger, the blood being cooled down to a temperature in the range 10° C. to 30° C.;
    thereafter, passing the cooled blood through the dialysis device;
    providing a second heat exchanger for warming the blood up to a temperature at least near to a body temperature of the patient; and then
    returning the warmed blood to the patient's body, such that said method defines a continuous circuit for heparin-free reduction of blood coagulation,
    wherein the first heat exchanger is placed before the dialysis device and is connected with a circuit of a cooling medium, and
    the second exchanger is placed after the dialysis device and is connected to a circuit of a heating medium,
    wherein both the cooling medium and the heating medium circuits are connected with the outputs of a control unit,
    wherein, before said first heat exchanger, a cooling input temperature sensor is disposed along the cooling medium circuit and, after the first heat exchanger, a cooling output temperature sensor is disposed along the cooling medium circuit, wherein outputs of the cooling input and cooling output temperature sensors are connected with the control unit.

2. A method according to claim 1, further comprising providing, at the output of blood out of the first heat exchanger, a blood outlet temperature sensor, the output of which is also connected with the control unit.

3. A system for heparin-free reduction of blood coagulation comprising:
    a kidney dialysis device including a continuous extracorporeal circuit;
    a control unit;
    a first heat exchanger placed before the dialysis device and connected with a circuit of a cooling medium, and
    a second exchanger placed after the dialysis device and connected to a circuit of a heating medium,
    wherein both the cooling medium and the heating medium circuits are connected with the outputs of a control unit,
    the system further comprising a cooling input temperature sensor disposed before said first heat exchanger and along said cooling medium circuit and a cooling output temperature sensor disposed after the first heat exchanger and disposed along the cooling medium circuit, wherein an output of the cooling input and cooling output temperature sensors are connected with the control unit.

4. A method according to claim 1, wherein the first heat exchanger is located near to the outlet of blood from the patient's body.

5. The method according to claim 1, wherein the dialysis device, the first heat exchanger and the second exchanger are present in a single continuous extracorporeal blood circuit, and wherein the method is performed using a system consisting of only one continuous extracorporeal blood circuit.

6. The method according to claim 1, further comprising providing a blood inlet temperature sensor located on the inlet of blood from the patient's body to said first heat exchanger, wherein an output of the blood inlet temperature sensor is connected with the control unit.

7. The system according to claim 3, further comprising a blood inlet temperature sensor located on the inlet of blood from the patient's body to said first heat exchanger, wherein an output of the blood inlet temperature sensor is connected with the control unit.

8. The system according to claim 3, wherein the dialysis device, the first heat exchanger and the second exchanger are present in a single continuous extracorporeal blood circuit, and wherein the system consists of only one continuous extracorporeal blood circuit.

9. The system according to claim 3, further comprising a blood inlet temperature sensor located on an inlet of blood to said first heat exchanger.

10. The system according to claim 9, further comprising, a blood outlet temperature sensor disposed at an output of blood out of said first heat exchanger, an output of said blood outlet temperature sensor being connected with the control unit.

* * * * *

UNITED STATES PATENT AND TRADEMARK OFFICE
CERTIFICATE OF CORRECTION

PATENT NO. : 8,529,489 B2
APPLICATION NO. : 12/320276
DATED : September 10, 2013
INVENTOR(S) : Jiri Ruzicka et al.

Page 1 of 1

It is certified that error appears in the above-identified patent and that said Letters Patent is hereby corrected as shown below:

Title Page, Item (75) Inventors: Correct -- The first inventor's citizenship to CZ --.

Signed and Sealed this
Twelfth Day of November, 2013

Teresa Stanek Rea
*Deputy Director of the United States Patent and Trademark Office*